(12) United States Patent
Fujita et al.

(10) Patent No.: US 10,843,191 B2
(45) Date of Patent: Nov. 24, 2020

(54) MOLECULE DETECTING SYSTEM

(71) Applicant: Centre National de la Recherche Scientifique (CNRS), Paris (FR)

(72) Inventors: Hiroyuki Fujita, Tokyo (JP); Mehmet Cagatay Tarhan, Tokyo (JP); Nicolas Lafitte, Tokyo (JP); Dominique Collard, Tokyo (JP)

(73) Assignee: Centre National de la Recherche Scientifique (CNRS), Paris (FR)

( * ) Notice: Subject to any disclaimer, the term of this patent is extended or adjusted under 35 U.S.C. 154(b) by 583 days.

(21) Appl. No.: 15/527,866

(22) PCT Filed: Nov. 20, 2015

(86) PCT No.: PCT/JP2015/082789
§ 371 (c)(1),
(2) Date: Oct. 23, 2018

(87) PCT Pub. No.: WO2016/080543
PCT Pub. Date: May 26, 2016

(65) Prior Publication Data
US 2019/0046981 A1    Feb. 14, 2019

(30) Foreign Application Priority Data

Nov. 21, 2014    (JP) .................................. 2014-236193

(51) Int. Cl.
*C12Q 1/6825*    (2018.01)
*C12Q 1/689*    (2018.01)
(Continued)

(52) U.S. Cl.
CPC ... *B01L 3/502715* (2013.01); *B01L 3/502746* (2013.01); *B01L 3/502761* (2013.01);
(Continued)

(58) Field of Classification Search
CPC ......... B01L 3/502715; B01L 3/502761; B01L 3/502746; B01L 9/527; B01L 2200/0663;
(Continued)

(56) References Cited

U.S. PATENT DOCUMENTS

2007/0023621 A1    2/2007    Blick et al.
2014/0150522 A1    6/2014    Glasgow et al.

FOREIGN PATENT DOCUMENTS

JP    2006-312211 A    11/2006
JP    2012-080791 A    4/2012
(Continued)

OTHER PUBLICATIONS

Kumemura, et al., Direct Bio-Mechanical Sensing of Enzymatic Reaction on DNA by Silicon Nanotweezers, 2010, IEEE, p. 915-918, DOI: 10.1109/MEMSYS.2010.5442356 (Year: 2010).*

(Continued)

*Primary Examiner* — Jennifer Wecker
*Assistant Examiner* — Michael Paul Shimek
(74) *Attorney, Agent, or Firm* — Banner & Witcoff, Ltd.

(57) ABSTRACT

An object is to stably, continuously and easily detect reactions of filamentary biomolecules or polymers bridging between a pair of electrodes against reagents without employing any marker or labeling substances. A molecule detecting system for detecting a reaction of a molecule captured between electrodes to a reagent in a liquid 37, the system comprising: a detection device including a couple of electrodes and being capable of measuring a resonance frequency and an amplitude of the electrodes; a microfluidic device 30 including a microfluidic channel 36 which includes a channel opening 36c on its one side, wherein an air-liquid interface the electrodes can pass through is formed in the channel opening 36c; a pressure controlled microfluidic pump 33 connected to an outlet 36b of the microfluidic (Continued)

channel 36; a movable holding device movably holding the detection device or the microfluidic device 30; and a controller controlling the detection device, the pressure controlled microfluidic pump 33, and the movable holding device.

9 Claims, 11 Drawing Sheets

(51) Int. Cl.
| | | |
|---|---|---|
| *G01N 11/00* | (2006.01) | |
| *G01N 11/16* | (2006.01) | |
| *G01N 19/00* | (2006.01) | |
| *B01L 3/00* | (2006.01) | |
| *G01N 33/487* | (2006.01) | |
| *B01L 9/00* | (2006.01) | |

(52) U.S. Cl.
CPC .............. *B01L 9/527* (2013.01); *C12Q 1/689* (2013.01); *C12Q 1/6825* (2013.01); *G01N 11/00* (2013.01); *G01N 11/16* (2013.01); *G01N 19/00* (2013.01); *G01N 33/48721* (2013.01); *B01L 2200/0663* (2013.01); *B01L 2300/0645* (2013.01); *B01L 2300/0809* (2013.01); *B01L 2300/14* (2013.01)

(58) Field of Classification Search
CPC ......... B01L 2300/0809; B01L 2300/14; B01L 2300/0645; G01N 19/00; G01N 11/00; G01N 11/16; G01N 33/48721; C12Q 1/6825; C12Q 1/689
See application file for complete search history.

(56) References Cited

FOREIGN PATENT DOCUMENTS

| JP | 2013-210387 A | 10/2013 |
|---|---|---|
| WO | 00/68419 A2 | 11/2000 |
| WO | 2010/144157 A1 | 12/2010 |
| WO | 2014/018558 A1 | 1/2014 |
| WO | 2014/072397 A1 | 5/2014 |
| WO | 2014069551 A1 | 5/2014 |

OTHER PUBLICATIONS

Jun. 21, 2018 (EP) Supplementary European search report issued for the corresponding European patent application EP15861543.5.

Tarhan et al. A rapid and practical technique for real-time monitoring of biomolecular interactions using mechanical responses of macromolecules. Scientific Reports, 6:28001, DOI: 10.1038/srep28001.

Kumemura M. et al., "Direct bio-mechanical sensing of enzymatic reaction on DNA by silicon nanotweezers", Proc. IEEE MEMS, 2010, pp. 915-918.

Lafitte N. et al., "Real-time sensing of molecule binding on DNA with silicon nanotweezers", Proc. MicroTAS, 2011, pp. 389-391.

Chiang, Po-Tsun et al., "Real-time measurement of DNA degradation under radiation by silicon nanotweezers coupled with microfluidic cavity", the Papers of Technical Meeting on Bio Micro Systems, IEE Japan/the Institute of Electrical Engineers of Japan, May 27, 2014, pp. 67-72.

\* cited by examiner (a)

(b)

MOLECULE DETECTING SYSTEM

RELATED APPLICATIONS

This application is a National Stage Application under 35 U.S.C. 371 of PCT application PCT/JP2015/082789 designating the United States and filed Nov. 20, 2015; which claims the benefit of JP application number 2014-236193 and filed Nov. 21, 2014 each of which are hereby incorporated by reference in their entireties.

TECHNICAL FIELD

The present invention relates to a molecule detecting system.

BACKGROUND ART

Hitherto, for detecting DNA etc., methods using DNA chips and those using Surface Plasmon Resonance (SPR) have been widely adopted (see, for example, Patent Documents 1 and 2).

In the methods using DNA chips, DNAs of a variety of sequences can be identified at high throughputs through detection based on complementary binding of DNAs attached on chips for detection and sample DNAs. In the methods using Surface Plasmon Resonance, binding of molecules can be detected at high sensitivities.

CITATION LIST

Patent Document 1: Japanese Patent Application Laid-Open (kokai) No. 2012-080791 (JP 2012-080791 A)
Patent Document 2: Japanese Patent Application Laid-Open (kokai) No. 2013-210387 (JP 2013-210387 A)

SUMMARY OF INVENTION

Problems to be Solved by Invention

However, in the aforementioned conventional methods, many problems are included. In the methods using DNA chips, fluorescent substances are needed to be attached onto DNAs and devices for detection fluorescent images are necessary. Another one is a problem of low data reliability. In the methods using Surface Plasmon Resonance, large scale catoptric systems are necessary. Another problem is that observable reactions just occur in so thin layers of liquid, about a hundred [nm] in thickness (depth), that Plasmon can appear on substrate surfaces.

An object of the present invention is to solve the above-mentioned problems in the conventional method and to provide a molecule detecting system, in which reactions of filamentary biomolecules or polymers bridging between a pair of electrodes against reagents are stably, continuously and easily detected without employing any marker or labeling substances.

Means for Solving Problems

Accordingly, the present invention provides a molecule detecting system for detecting a reaction of a molecule captured between electrodes to a reagent in a liquid, the system comprising: a detection device including a couple of electrodes and being capable of measuring a resonance frequency and an amplitude of the electrodes; a microfluidic device including a microfluidic channel which includes a channel opening on its one side, wherein an air-liquid interface the electrodes can pass through is formed in the channel opening; a pressure controlled microfluidic pump connected to an outlet of the microfluidic channel; a movable holding device movably holding the detection device or the microfluidic device; and a controller controlling the detection device, the pressure controlled microfluidic pump, and the movable holding device.

In another molecule detecting system of the present invention, the detection device is capable of varying a distance between the electrodes at a predetermined frequency.

In yet another molecule detecting system of the present invention, the electrodes can be moved relatively to the channel opening by the movable holding device moving the detection device or the microfluidic device, so that the electrodes are immersed in and pulled out from the liquid in the microfluidic channel through the air-liquid interface.

In yet another molecule detecting system of the present invention, the controller decides and memorizes an in-liquid position, in which the electrodes are in the liquid, and an in-air position, in which the electrodes are out of the liquid, through a positioning operation processed beforehand.

In yet another molecule detecting system of the present invention, the controller decides the in-liquid position and the in-air position based on a change of the amplitude of the electrodes.

In yet another molecule detecting system of the present invention, the pressure controlled microfluidic pump withdraws the liquid in the microfluidic channel from the outlet, so that another liquid is brought in the microfluidic channel from an inlet of the microfluidic channel.

In yet another molecule detecting system of the present invention, the controller makes the liquid in the microfluidic channel altered for another liquid in turns.

In yet another molecule detecting system of the present invention, the controller makes a measurement of the resonance frequency and the amplitude continued, with keeping the electrodes, which capture the molecule, in the liquid, and memorizes a result of the measurement.

In yet another molecule detecting system of the present invention, the controller calculates a stiffness and a damping of the molecule based on the result of the measurement.

Effects of Invention

According to the present invention, reactions of filamentary biomolecules or polymers bridging between a pair of electrodes upon reagents are stably, continuously and easily detected without employing any marker or labeling substances.

DESCRIPTION OF EMBODIMENTS

An embodiment of the present invention will next be described in detail with reference to the drawings.

Figure 1:
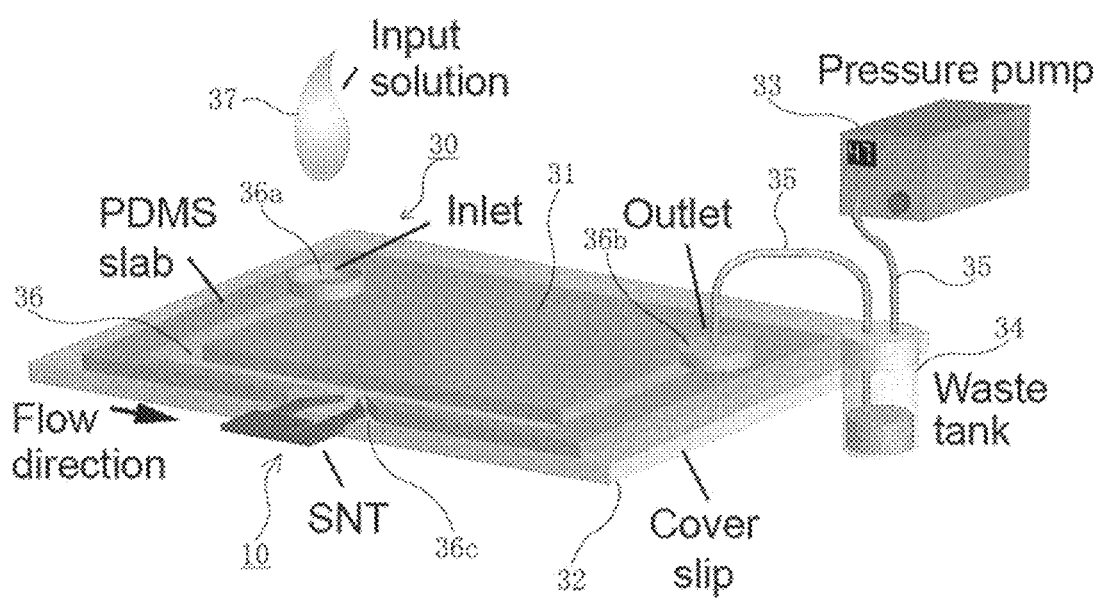
FIG. 1 is a perspective view showing a microfluidic device and a nano-tweezers according to an embodiment of the present invention.
Figure 2:
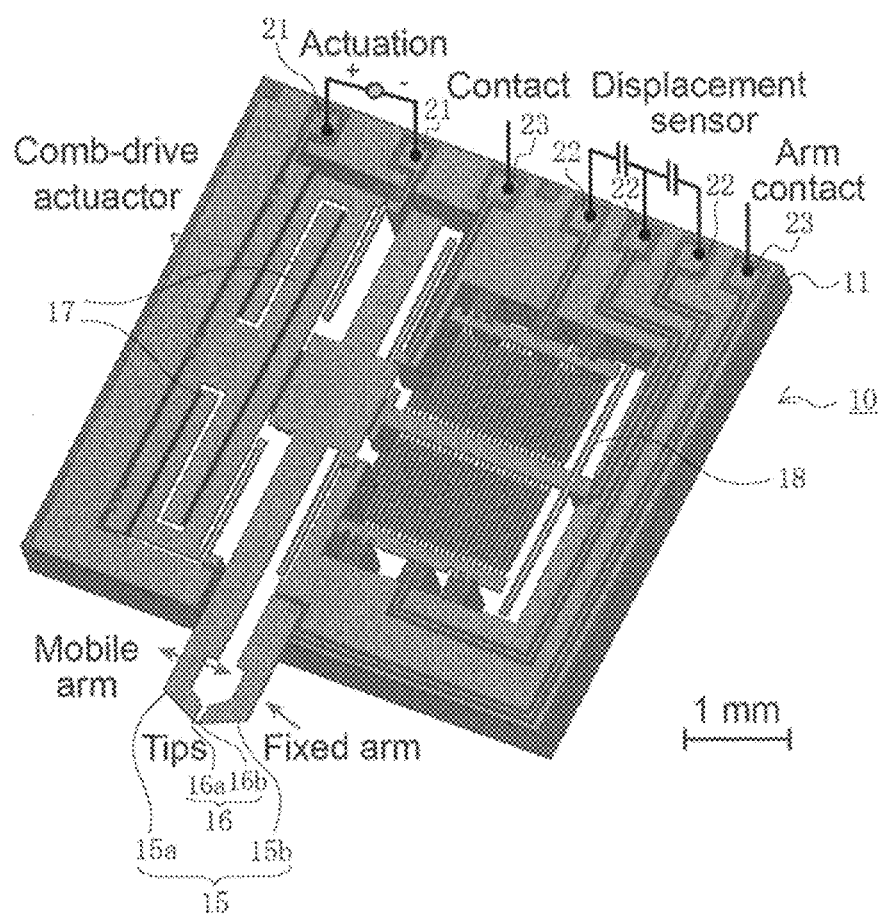
FIG. 2 is a perspective view showing the nano-tweezers according to the embodiment of the present invention.
Figure 3:
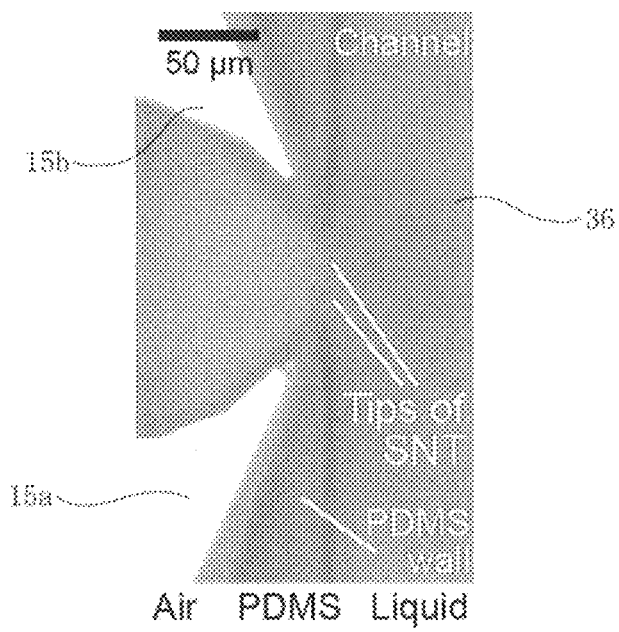
FIG. 3 is a photograph showing a situation where tips of arm members of the nano-tweezers are immersed in a microfluidic channel of the microfluidic device according to the embodiment of the present invention.
Figure 4:
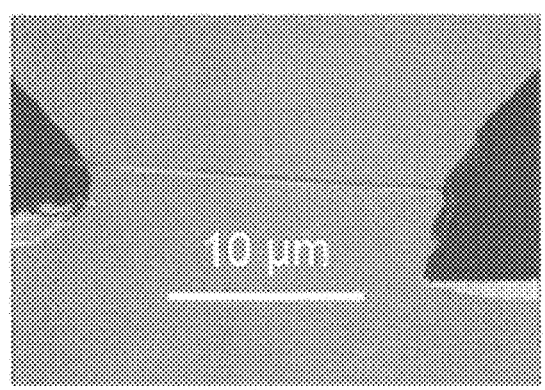
FIG. 4 is a photograph showing a DNA bridging between the tips of arm members of the nano-tweezers according to the embodiment of the present invention.
Figure 5:
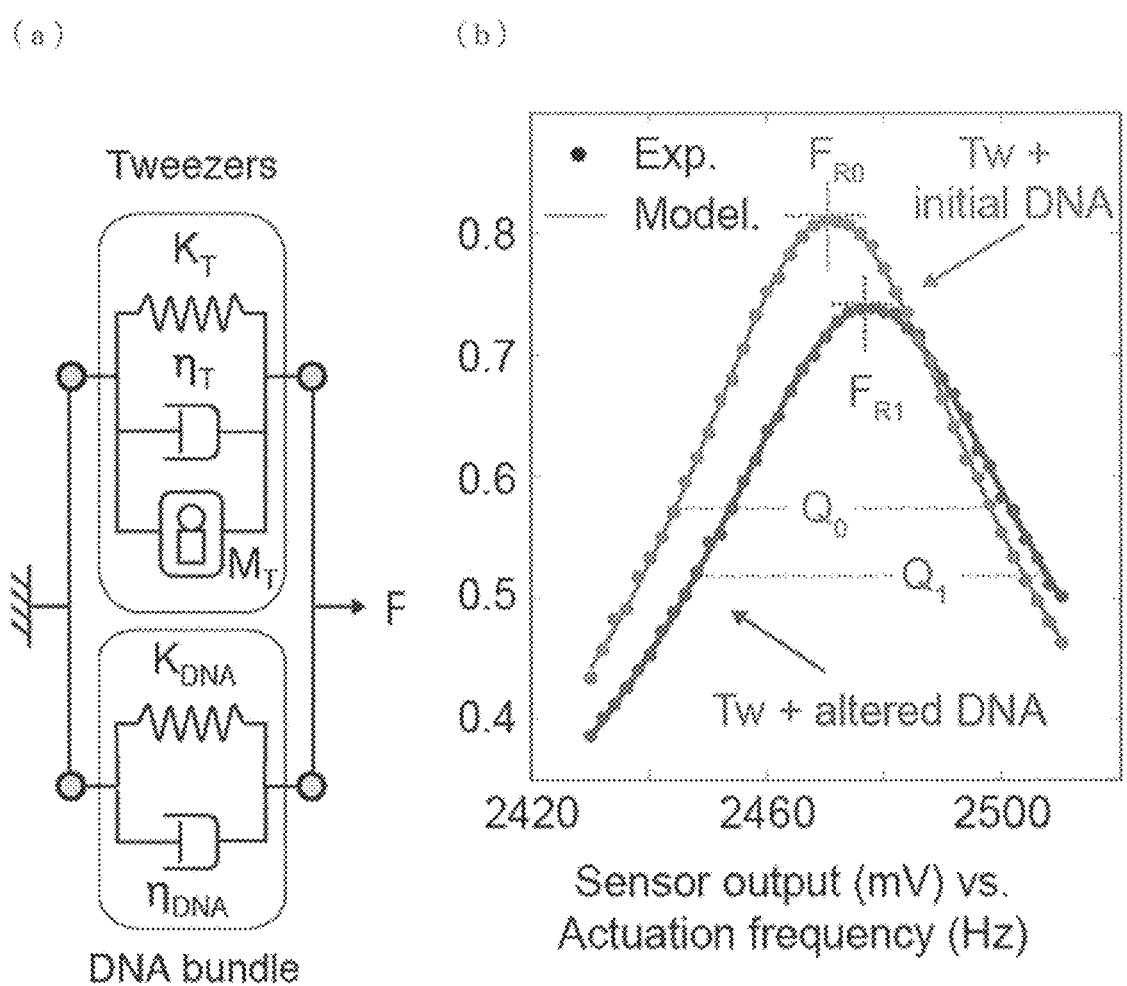
FIG. 5 is a set of views illustrating a method of characterizing the DNA bridging between the tips of arm members of the nano-tweezers according to the embodiment of the present invention.

FIG. 1 is a perspective view showing a microfluidic device and a nano-tweezers according to the embodiment of the present invention. FIG. 2 is a perspective view showing the nano-tweezers according to the embodiment of the present invention. FIG. 3 is a photograph showing a situation where tips of arm members of the nano-tweezers are immersed in a microfluidic channel of the microfluidic device according to the embodiment of the present invention. FIG. 4 is a photograph showing a DNA bridging between the tips of arm members of the nano-tweezers according to the embodiment of the present invention. FIG. 5 is a set of views illustrating a method of characterizing the DNA bridging between the tips of arm members of the nano-tweezers according to the embodiment of the present invention. In FIG. 5, (a) shows an equivalent circuit of the DNA bridging between the tips of arm members and (b) is a graph showing a resonance frequency shift.

In the respective figures, a reference numeral 30 designates a microfluidic device in the present embodiment, and a reference numeral 10 designates a nano-tweezers (a silicon nano-tweezers: SNT), as a detection device employed in the present embodiment.

The microfluidic device 30 includes a base board 32 made from a coverslip, which is a transparent glass plate, and a PDMS (poly-dimethyl-siloxane) film 31 attached onto a surface of the base board 32. In the PDMS film 31, a microfluidic channel 36, having a shape like the letter "U" in a plan view, is formed. An inlet 36a and an outlet 36b are formed on both ends of the microfluidic channel 36, and a channel opening 36c is formed on a side of its straight middle section. Liquid 37 is supplied from the inlet 36a, flows in the microfluidic channel 36 in a direction shown by an arrow, and is discharged from the outlet 36b.

The PDMS film 31 can be produced with utilizing a known photolithographic technology (see, for example, Patent Document 3). The PDMS film 31 may be replaced by a film made from other polymers or glasses, such as Pyrex®, etc. or also may be fabricated by other methods, such as hot embossing, drilling, etc.

Patent Document 3: Japanese Patent Application Laid-Open (kokai) No. 2006-312211 (JP 2013-312211 A)

A pressure controlled microfluidic pump 33 is connected to the outlet 36b of the microfluidic channel 36 via exhaust pipes 35 and a waste tank 34 connected between the exhaust pipes 35. As the pressure controlled microfluidic pump 33 withdraws the existing liquid 37 from the microfluidic channel 36 and brings it into the waste tank 34, another kind of liquid 37 can be brought in the microfluidic channel 36 from the inlet 36a. In another word, the pressure controlled microfluidic pump 33 can change the liquid 37 in the microfluidic channel 36. The pressure can be altered depending on the desired flow rate that is detected with the flow sensor integrated into the pressure controlled microfluidic pump 33.

The present inventors used, as the pressure controlled microfluidic pump 33, a set of "AF1 Dual Vacuum & Pressure Generator", "Vacuum & Pressure Controller" and a "flow-sensor" produced by "Elveflow". This product set is a pump set used for devices handling micro-fluid and a stable flow without pulsation can be achieved by using this product. The pressure range of this product is − (minus) 700 [mbar]−1 [bar].

The nano-tweezers 10 is a device produced from a silicon substrate by MEMS technology and has a structure similar to the nano-tweezers shown in Non-Patent Documents 1 and 2.

Non-Patent Document 1: M. Kumemura, D. Collard, S. Yoshizawa, D. Fourmy, N Lafitte, S. Takeuchi, T. Fujii, L. Jalabert, and H. Fujita, "Direct bio-mechanical sensing of enzymatic reaction on DNA by silicon nanotweezers," Proc. IEEE MEMS '10, pp. 915-918, 2010

Non-Patent Document 2: N. Lafitte, M. Kumemura, L. Jalabert, D. Collard, and H. Fujita, "Real-time sensing of molecule binding on DNA with silicon nanotweezers," Proc. MicroTAS 2011, 389-391

As illustrated in FIG. 2, the nano-tweezers 10 includes a main body 11, with a form of plate in a rectangular plane shape, and a pair of arm members 15 protruding in parallel each other from a side of the main body 11. The arm members 15 consist of a moving arm 15a and a fixed arm 15b, the former of which is attached to the main body 11 in a movable or displaceable manner and the latter of which is attached to the main body 11 in an immovable manner. The moving arm 15a and the fixed arm 15b are configured in side by side on a plane parallel to the surface of the main body 11, and the moving arm 15a moves on the plane parallel to the surface of the main body 11.

A moving tip part 16a in a sharp-pointed shape is formed at the tip of the moving arm 15a, and a fixed tip part 16b in a sharp-pointed shape is formed at the tip of the fixed arm 15b. The moving tip part 16a and the fixed tip part 16b are opposing each other. The moving tip part 16a and the fixed tip part 16b will be described as tip parts 16 when it would be better to explain them altogether. The tip parts 16 function as electrodes and designated AC voltage is impressed between them. At least a part of the surface of the tip parts 16 is desirably coated with gold or aluminum.

The main body 11 includes a comb-drive actuator 17 for displacing the moving arm 15a. The comb-drive actuator 17 is a linear actuator utilizing an electrostatic force acting between non graphically illustrated conductive comb teeth, and can displace the moving arm 15a in a direction orthogonal to its major axis, as shown by a two-directional arrow in FIG. 2, to adjust a gap between the moving arm 15a and the fixed arm 15b. Thereby, a gap between the tip parts 16, that is, between the moving tip part 16a and the fixed tip part 16b, can be varied.

The main body 11 also includes a displacement sensor 18 for measuring an amount of displacement of the moving arm 15a. The displacement sensor 18 is a capacitive sensor detecting capacitance variation, and can measure displacement of the moving arm 15a. Thereby, a gap and a gap variation between the tip parts 16, that is, between the moving tip part 16a and the fixed tip part 16b, can be measured. Also, a resonance frequency and an amplitude of vibration of the tip parts 16 can be measured.

On the surface of the main body 11, actuator terminals 21 for applying an electric voltage to the comb-drive actuator 17, sensor terminals 22 for detecting capacitance variation of the displacement sensor 18, and arm member terminals 23 for impressing AC voltage between the tip parts 16 on tips of the pair of arm members 15 are provided.

The nano-tweezers 10 is used with the microfluidic device 30. Specifically, as illustrated in FIG. 3, the tip parts 16 of the arms 15 are inserted into the channel opening 36c to pass through an air-liquid interface formed in the channel opening 36c and to arrive in the microfluidic channel 36. A white dotted line, shown in FIG. 3, indicates the air-liquid interface, a boundary between the liquid 37 in the microfluidic channel 36 and an outside air. The air-liquid interface is in shape of meniscus because of capillary action.

By immersing the tip parts 16 of the arms 15 into a solution including filamentary biomolecules, such as DNA, or polymers, such as PLA (polylactide), in advance, molecules or molecule bundles of the biomolecules or the polymers form a bridge between the tip parts 16, as illustrated in FIG. 4. FIG. 4 illustrates a result of an experiment the present inventors carried out, and, from this result, it is clear that a bundle of λDNA was captured to form a bridge of λDNA between the tip parts 16.

After capturing the molecules between the tip parts 16 as described above, the comb-drive actuator 17 of the nano-tweezers 10 is operated to vary the gap between the moving tip part 16a and the fixed tip part 16b at a prescribed frequency and to vibrate the molecules bridging between the tip parts 16. Thereby, the molecules are characterized on real time by measuring their resonance frequency.

When the molecules or the molecule bundles of filamentary biomolecules (e.g. DNA, RNA, microtubule, actin, fibronectin, intermediate filament) or polymers (e.g. PLA) react upon reagents (e.g. complementary ss DNA, drug candidates, nanoparticles, enzymes) in the solution, their mechanical characteristics (e.g. stiffness, viscosity) alter their resonance characteristics. Therefore, processes of biochemical reactions of the molecules are continuously measured by measuring their resonance characteristics. For this reason, a stability of measurement during long time and a stability of repetitious measurements are necessary.

FIG. 5(b) illustrates a result of an experiment the present inventors have carried out with the nano-tweezers 10, which is a result of measuring the resonance frequencies and the amplitudes of the tip parts 16 capturing DNA. In FIG. 5(b), the horizontal axis indicates frequency [Hz] and the vertical axis indicates output voltage [mV] of sensor for measuring amplitude. An equivalent circuit of vibration system of the tip parts 16 capturing DNA can be illustrated as in FIG. 5(a). The resonance frequency is tracked by a phase-lock loop.

As illustrated in FIG. 5(b), it is clear that the resonance frequencies of the tip parts 16 are different when DNAs are different. Therefore, by measuring in advance the resonance frequencies of the tip parts 16 capturing plural kind of filamentary biomolecules, such as DNA, and polymers, such as PLA, it is possible to identify filamentary biomolecules and polymers captured between the tip parts 16.

Next will be described a system for controlling comparative positional relation between the nano-tweezers 10 and the microfluidic device 30. In this embodiment, it will be provided that the liquid 37 is the solution including biomolecules and polymers.

Figure 6:
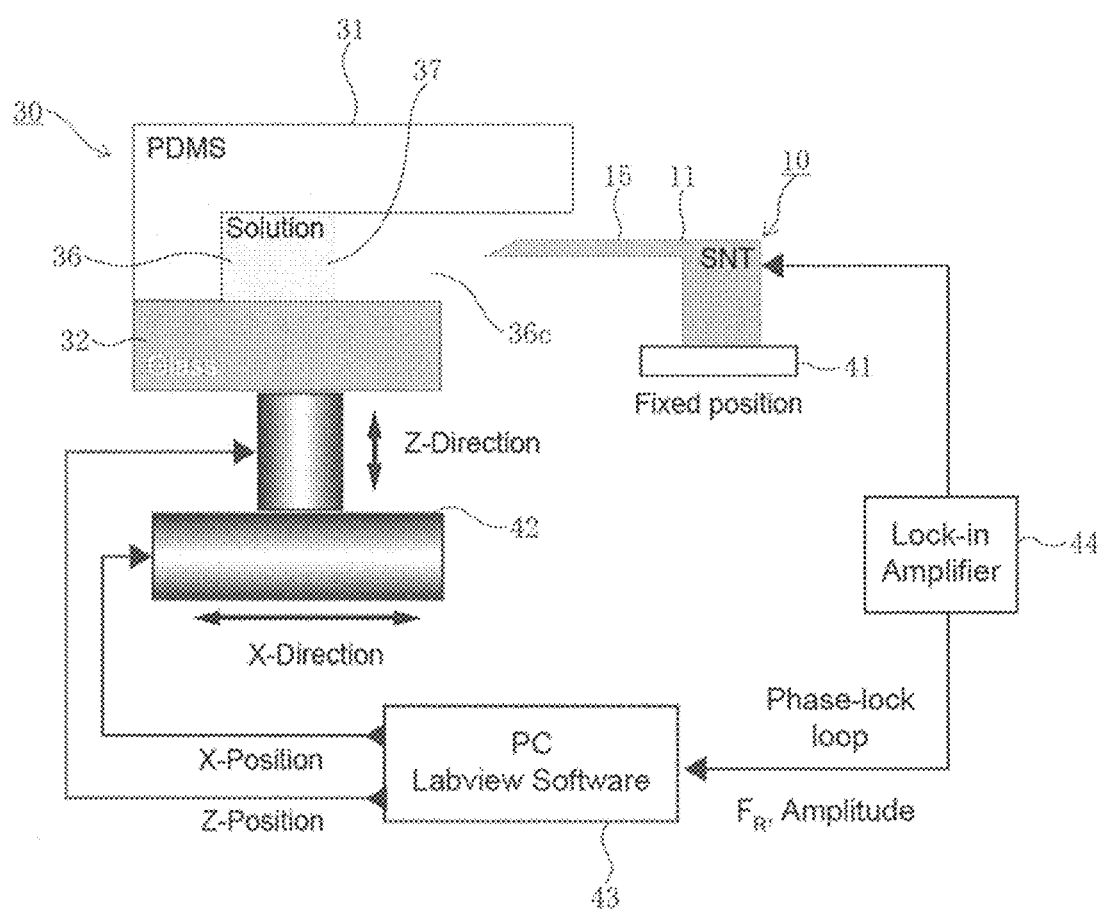
FIG. 6 is a schematic view showing a system for controlling positional relation between the nano-tweezers and the microfluidic device according to the embodiment of the present invention.
Figure 7:
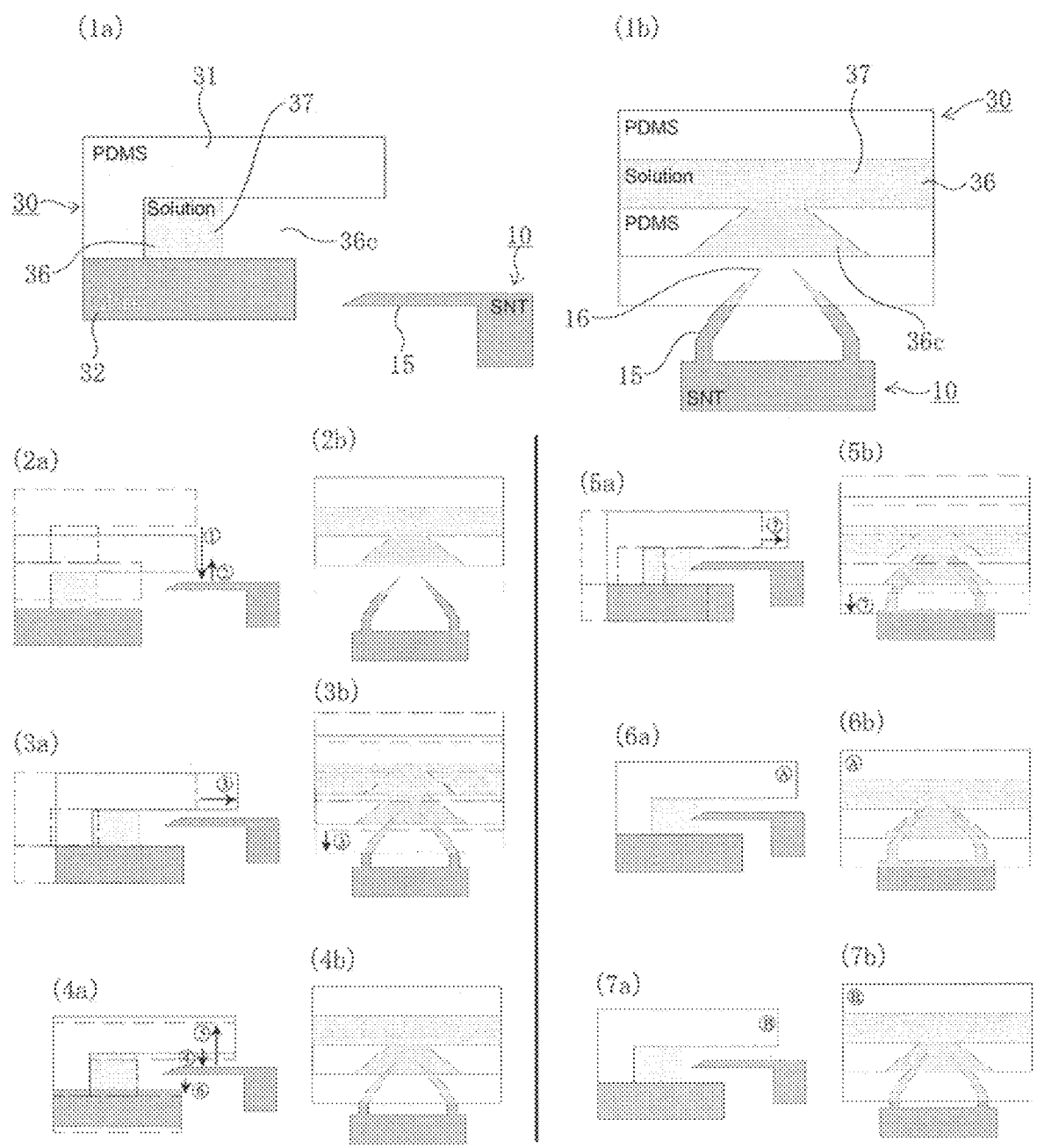
FIG. 7 is a schematic view showing changes of positional relation between the nano-tweezers and the microfluidic device according to the embodiment of the present invention.

FIG. 6 is a schematic view showing a system for controlling positional relation between the nano-tweezers and the microfluidic device according to the embodiment of the present invention. FIG. 7 is a schematic view showing changes of positional relation between the nano-tweezers and the microfluidic device according to the embodiment of the present invention. In FIG. 7, each of (1a)-(7a) shows a side view at each positional relation and each of (1b)-(7b) shows a plan view at each positional relation.

As illustrated in FIG. 6, the nano-tweezers 10 is attached onto a plane top surface of a non-movable holding device 41, which is fixed onto a laboratory floor etc. so that the surface of the main body 11 becomes horizontal. Thereby, the arm members 15 are at the same level.

The microfluidic device 30 is attached onto a top plane of a movable holding device 42, which is fixed onto a base opposing to the non-movable holding device 41, so that the base board 32 becomes horizontal. The movable holding device 42 can automatically displace the microfluidic device 30 in Z direction (vertical direction) and in X direction (direction in which the microfluidic device 30 closes to or leave from the nano-tweezers 10 in the level plane: up-down direction in FIG. 7 (1b)). While it is possible to attach the nano-tweezers 10 onto the movable holding device 42 and to attach the microfluidic device 30 onto the non-movable holding device 41, just the example in which the nano-tweezers 10 is attached onto the non-movable holding device 41 and the microfluidic device 30 is attached onto the movable holding device 42 will be described in this embodiment.

The operation of the movable holding device 42 is controlled by a controller 43, such as a personal computer (PC), etc. Thereby, a Z direction position and a X direction position of the microfluidic device 30 is automatically adjusted. A Y direction (direction orthogonal to Z and X directions: lateral direction in FIG. 7 (1b)) position of the microfluidic device 30 is manually adjustable. Lab VIEW software is installed in the controller 43. And, in order to monitor the resonance frequencies, the phase-lock loop including a lock-in amplifier 44 is connected to the controller 43, so that a FR amplitude of vibration of the arm members 15 is input into the controller 43.

As illustrated in FIG. 6, the movable holding device 42 is controlled by the controller 43, so that a positioning of the channel opening 36c of the microfluidic channel 36 of the microfluidic device 30 on the tip parts 16 of the arm members 15 of the nano-tweezers 10 is processed.

Next will be described a positioning operation processed beforehand in order to decide an in-liquid position, where the tip parts 16 is in the liquid 37, and an in-air position, where the tip parts 16 is out of the liquid 37. Positioning in Y direction is manually processed. Also positioning in X and Z directions to an initial position shown in FIG. 7 (1a) is manually processed.

Then, the microfluidic device 30 is descended in Z direction step by step, at each step of 1 [μm], as shown by an arrow (1) in FIG. 7 (2a), from the initial position to a position where the PDMS film 31 touches the arm members 15 of the nano-tweezers 10. Touch of the PDMS film 31 on the arm members 15 is detected by the controller 43 based on a sudden change in the amplitude of vibration of the arm members 15 (e.g. decrease of the amplitude to below 50 [%] of its maximum), which is monitored by the phase-lock loop.

When touch of the PDMS film 31 on the arm members 15 is detected, the microfluidic device 30 is ascended 50 [μm] in Z direction, as shown by an arrow (2) in FIG. 7 (2a). Thereby, the channel opening 36c of the microfluidic channel 36 is positioned in the vicinity of the tip parts 16 of the arm members 15 in Z direction.

Then, the microfluidic device 30 is moved a predetermined distance in X direction closer to the nano-tweezers 10, as shown by an arrow (3) in FIGS. 7 (3a) and (3b). The predetermined distance is variable due to the design of the microfluidic device 30 and is 200 [μm] for the microfluidic device 30 the present inventors used. Thereby, the tip parts 16 of the arm members 15 is positioned in the channel opening 36c of the microfluidic channel 36 though is still out of the microfluidic channel 36. That is, as illustrated in FIGS. 7 (3a) and (3b), the tip parts 16 of the arm members 15 is positioned between the PDMS film 31 and the base board 32 but not inserted in the liquid 37.

Then, in order to decide an accurate position in Z direction, the microfluidic device 30 is descended in Z direction, as shown by an arrow (4) in FIG. 7 (4a), until the PDMS film 31 touches the arm members 15 of the nano-tweezers 10. When the PDMS film 31 touches the arm members 15 of the nano-tweezers 10, the microfluidic device 30 is ascended in Z direction, as shown by an arrow (5), until the base board 32 touches the arm members 15 of the nano-tweezers 10. Touch of the base board 32 on the arm members 15 is detected, as mentioned above, based on a sudden change in the amplitude of vibration of the arm members 15. Thereby, the height of the microfluidic channel 36 and the position of the arm members 15 to the microfluidic channel 36 in Z direction are found. Then, the microfluidic device 30 is descended in Z direction, as shown by an arrow (6), until the distance between the base board 32 and the arm members 15 becomes a desired value.

Finally, the microfluidic device 30 is moved in X direction, as shown by an arrow (7) in FIGS. 7 (5a) and (5b), until the air-liquid interface touches the tip parts 16 of the arm members 15. Touch of the air-liquid interface on the tip parts 16 of the arm members 15 is detected based on a sudden change in the amplitude of vibration of the arm members 15. When the air-liquid interface touches the tip parts 16 of the arm members 15, the value of output voltage, shown as the vertical axis in FIG. 5 (b), usually increases by more than 0.2 [mV]. Thereby, the position of the arm members 15 to the air-liquid interface in X direction is found.

As described above, comparative positional relations between each part of the microfluidic device 30 and each part of the nano-tweezers 10, in directions X and Z, detected through the beforehand positioning operation process are memorized in a memory device of the controller 43. Then the in-liquid position, as shown in FIGS. 7 (6a) and (6b), and the in-air position, as shown in FIGS. 7 (7a) and (7b), are saved. The in-liquid position is a position which the tip parts 16 have reached after being inserted into the channel opening 36c of the microfluidic channel 36 and being immersed in the liquid 37 at a desired distance (depth) from the air-liquid interface. This distance from the air-liquid interface is preferably 5-10 [μm], according to experiments the present inventors accomplished. And, the in-air position is a position which the tip parts 16 of the arm members 15 have reached after being pulled out of the liquid 37 into the outside air at a desired distance from the air-liquid interface. This distance from the air-liquid interface is preferably 50 [μm], according to experiments the present inventors accomplished.

Next will be described contents and results of experiments the present inventors have accomplished using a molecule detecting system according to the present embodiment. First will be described an experiment to change the liquid 37 in the microfluidic channel 36.

Figure 8:
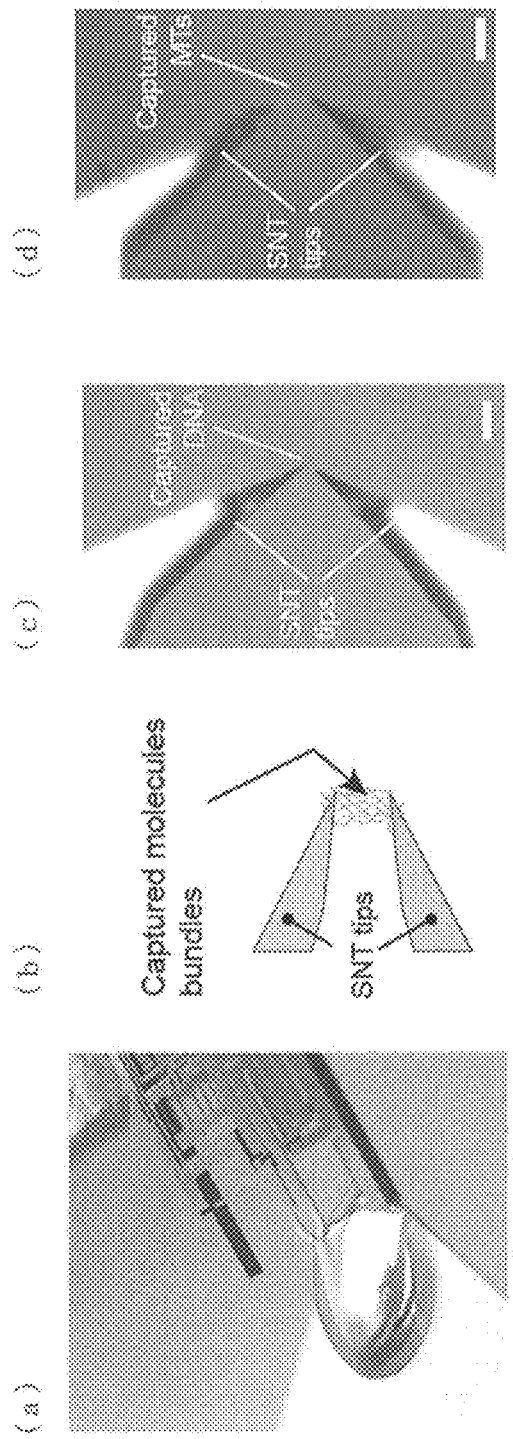
FIG. 8 is a set of views showing molecules bridging between the tips of arm members of the nano-tweezers according to the embodiment of the present invention.
Figure 9:
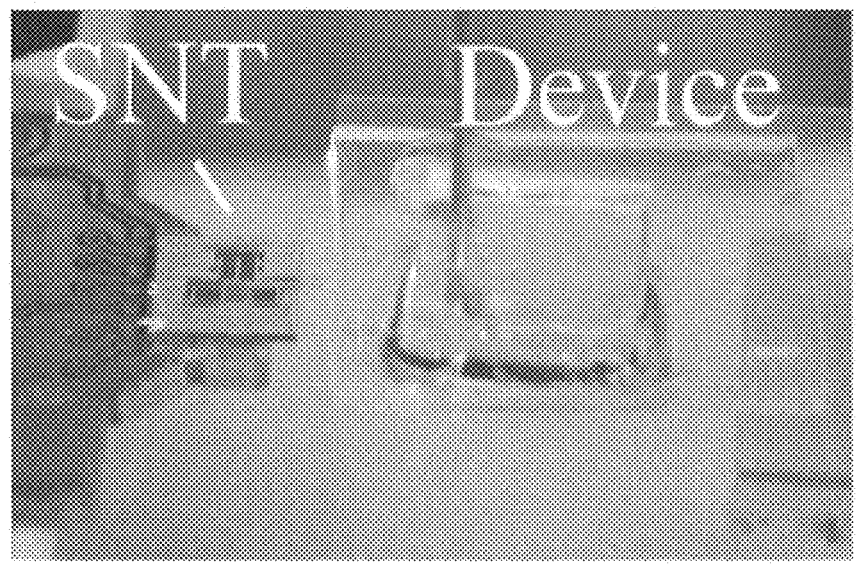
FIG. 9 is a photo showing a method for immersing the tip parts of the arm members of the nano-tweezers in the liquid in the microfluidic channel of the microfluidic device according to the embodiment of the present invention.
Figure 10:
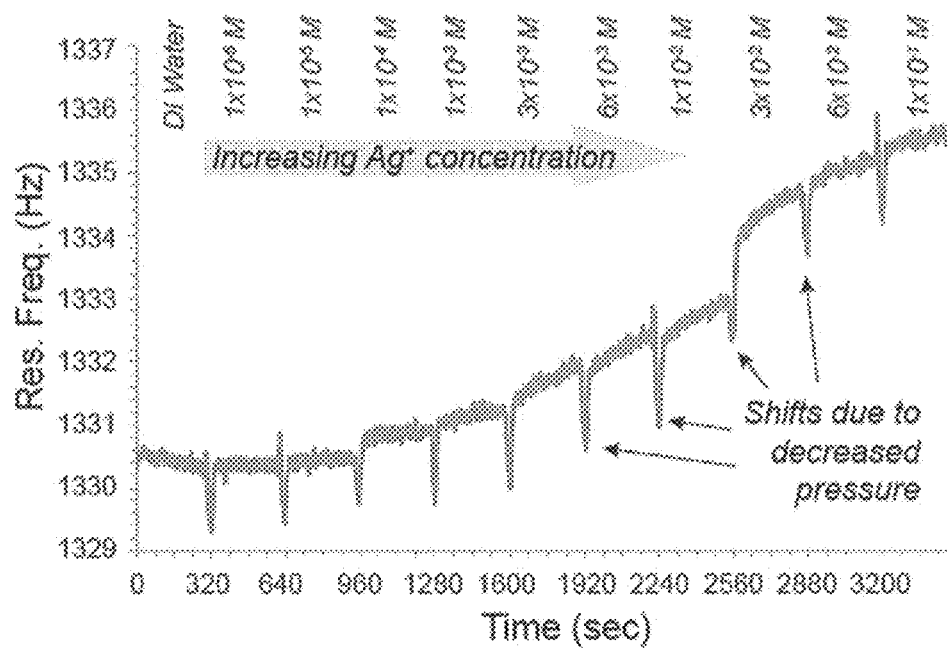
FIG. 10 is a first graph showing a resonance frequency shift in case of changing the liquid according to the embodiment of the present invention.
Figure 11:
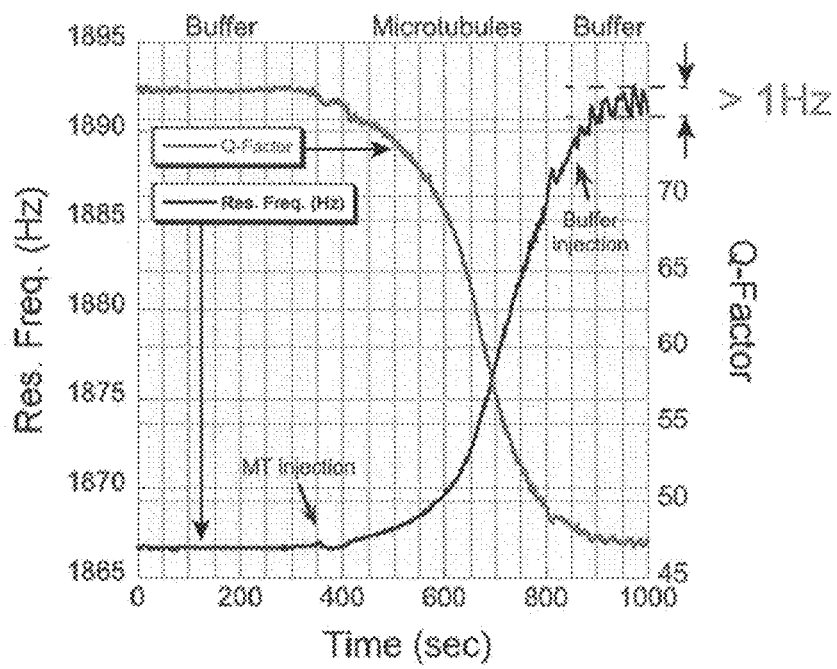
FIG. 11 is a graph showing a resonance frequency shift and Q-factor shift in case of changing the liquid according to an example for comparison.
Figure 12:
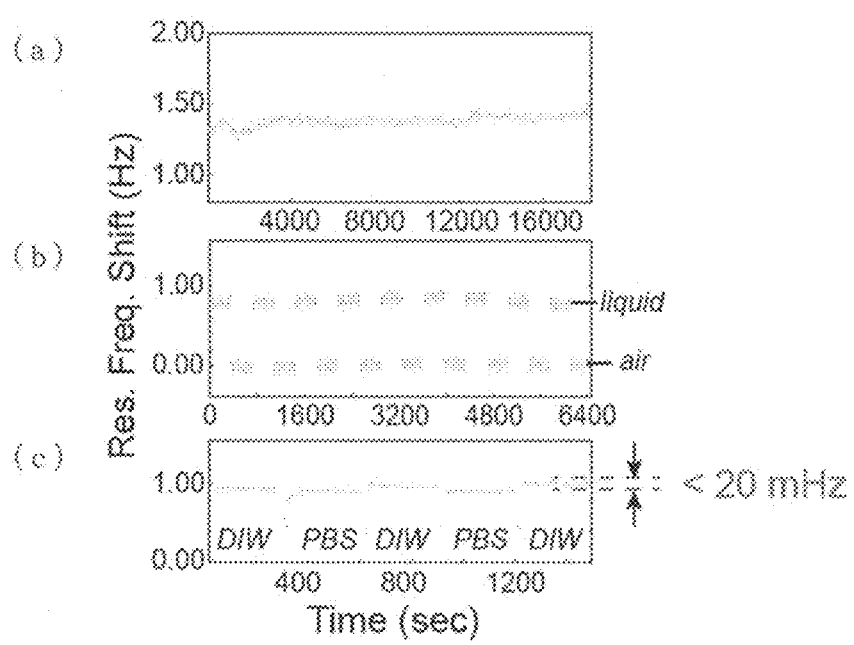
FIG. 12 is a set of graphs showing resonance frequency shifts according to the embodiment of the present invention.
Figure 13:
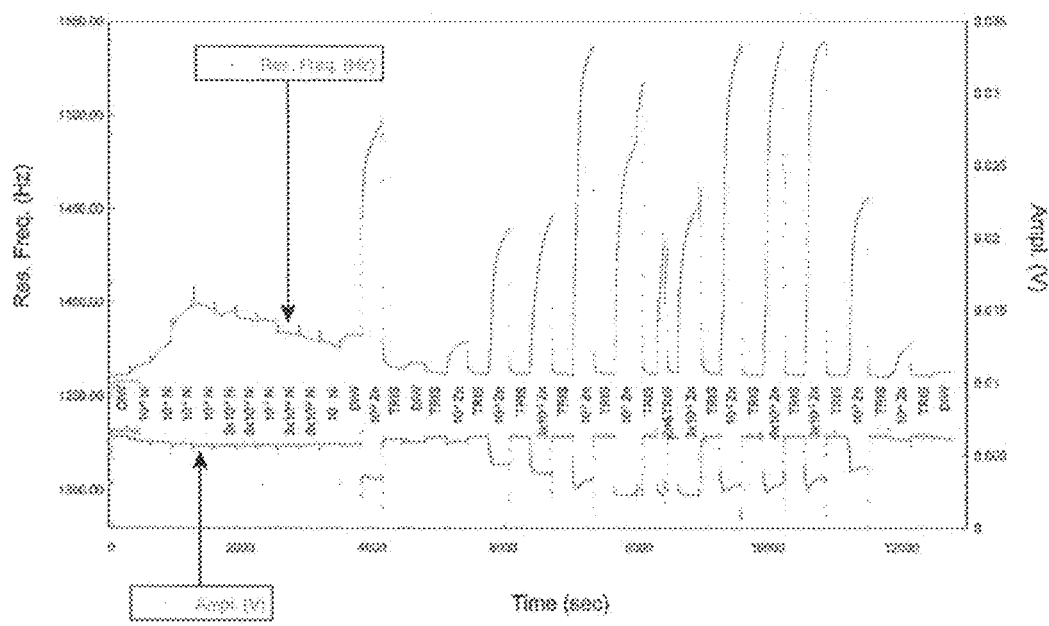
FIG. 13 is a set of second graphs showing resonance frequency shifts in case of changing the liquid according to the embodiment of the present invention.
Figure 13:
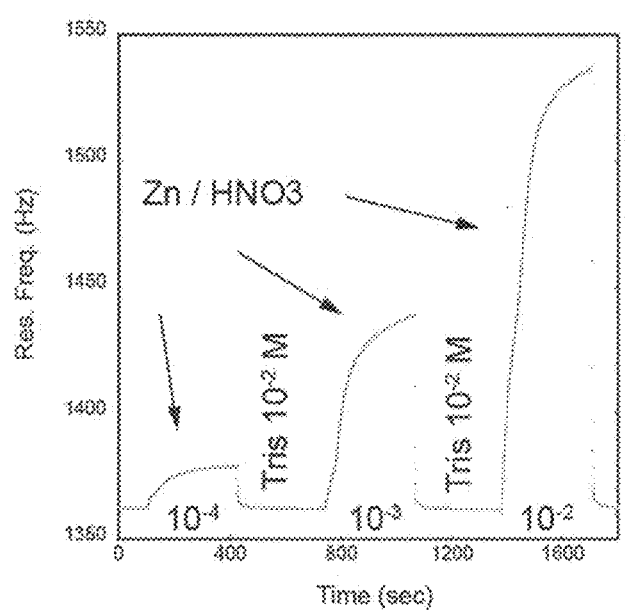

FIG. 8 is a set of views showing molecules bridging between the tips of arm members of the nano-tweezers according to the embodiment of the present invention. FIG. 9 is a photo showing a method for immersing the tip parts of the arm members of the nano-tweezers in the liquid in the microfluidic channel of the microfluidic device according to the embodiment of the present invention. FIG. 10 is a first graph showing a resonance frequency shift in case of changing the liquid according to the embodiment of the present invention. FIG. 11 is a graph showing a resonance frequency shift and Q-factor shift in case of changing the liquid according to an example for comparison. FIG. 12 is a set of graphs showing resonance frequency shifts according to the embodiment of the present invention. FIG. 13 is a set of second graphs showing resonance frequency shifts in case of changing the liquid according to the embodiment of the present invention. In FIG. 8, (a) is a photo of the tip parts of the arm members immersed in a droplet of liquid, (b) is a schematic view showing a molecule bundle bridging the tip parts of the arm members, (c) is a photo showing a DNA bridging the tip parts of the arm members, and (d) is a photo showing a microtubule bridging the tip parts of the arm members. In FIG. 12, (a) is a graph showing a resonance frequency shift measured for hours, (b) is a graph showing a resonance frequency shift in case the tip parts of the arm members in the "in-liquid" and the "in-air" positions, and (c) is a graph showing a resonance frequency shift in case changing the liquid. In FIG. 13, (a) is a graph showing a resonance frequency shift measured for hours, and (b) is a graph showing a resonance frequency shift in case changing concentration of solution.

The molecule detecting system according to the present embodiment includes the nano-tweezers 10, the microfluidic device 30, and the pressure controlled microfluidic pump 33 as shown in FIG. 1, and the movable holding device 42 and the controller 43 as shown in FIG. 6. The controller 43 preferably controls not only operation of the movable holding device 42 but also operations of the nano-tweezers 10 and the pressure controlled microfluidic pump 33, and memorizes measurement results, such as resonance frequencies and multitudes.

As shown in FIG. 8 (a), molecules are captured by immersing the tip parts 16 of the arm members 15 of the nano-tweezers 10 in a solution including molecules, such as biomolecules or polymers. The captured molecules, in bundle, bridge between the tip parts 16, as shown in FIG. 8 (b).

FIG. 8 (c) shows a case where the molecule captured and bridging between the tip parts 16 is a DNA. FIG. 8 (d) shows a case where the molecule captured and bridging between the tip parts 16 is a microtubule. Each of the bars indicated in FIGS. 8 (c) and 8 (d) is 10 [μm] in length.

FIG. 9 is a photo showing a positional relation between the nano-tweezers 10 and the microfluidic device 30, both of which have been really produced by the present inventors, and the photo illustrates a situation where the tip parts 16 of the armed members 15 of the nano-tweezers 10 is inserted in the channel opening 36c of the microfluidic channel 36 of the microfluidic device 30.

As mentioned above, in the molecule detecting system according to the present embodiment, comparative positional relations between each part of the microfluidic device 30 and each part of the nano-tweezers 10, in directions X and Z, are measured beforehand and are memorized in a memory device of the controller 43, so that the tip parts 16 of the arm members 15 can be automatically inserted in the channel opening 36c of the microfluidic channel 36. And the molecule detecting system according to the present embodiment employs the pressure controlled microfluidic pump 33 connected to the outlet 36b of the microfluidic channel 36. Thereby, in the molecule detecting system according to the present embodiment, molecules can be captured stably for hours and the liquids 37 in the microfluidic channel 36 can be changed stably and speedy, so that a variety of molecules can be characterized surely.

FIG. 10 illustrates a result of measurement the present inventors have accomplished with the molecule detecting system, and the result is the measured resonance frequencies of the case in which the tip parts 16 of the armed members 15, with λDNA bundles captured between the tip parts 16, have been immersed in solutions including Ag+ ions, the Ag+ ions have attached around the λDNA bundles, and the stiffness of the λDNA bundles have increased. In FIG. 10, the horizontal axis indicates the time [sec] elapsed from the beginning of measurement and the vertical axis indicates the resonance frequency [Hz].

In this measurement, the resonance frequency is continuously measured while the liquids 37 are altered every 320 [sec] elapsed. As shown in the upper part of FIG. 10, the liquid 37 for the first 320 [sec] is deionized water (DI water), the liquid 37 for the next 320 [sec] is Ag+ ion solution of $1\times10^{-6}$ M molarity concentration, then the liquid 37 is successively replaced with the Ag+ ion solutions of higher molarity concentration.

According to the result of measurement illustrated by FIG. 10, it is clear that, as the concentration of Ag+ ion in solutions increases, the stiffness of the λDNA bundles increases and the value of the resonance frequency [Hz] increases. The sudden drops every 320 [sec] in the result of measurement are due to pressure decreases in the microfluidic channel 36 when the liquids 37 are altered.

On the contrary, if the tip parts 16 of the arm members 15 are manually inserted in the channel opening 36c of the microfluidic channel 36, comparative positional relations in directions X and Z between the tip parts 16 of the arm members 15, and the channel opening 36c of the microfluidic channel 36 and the air-liquid interface would be different at every time of insertion, so that trouble would arise in stability, and capture or characterization of molecules would not be accomplished appropriately. Further, if the liquids 37 in the microfluidic channel 36 are changed by a widely used syringe pump connected to the inlet 36a and/or the outlet 36b of the microfluidic channel 36, trouble would arise in stability of the liquids 37 in the microfluidic channel 36 so that it would take some time for such processes as capturing or characterizing molecules, and trouble such as evaporation of liquids 37 at the inlet 36a, the outlet 36b or the channel opening 36c would arise so that capture or characterization of molecules would not be accomplished appropriately.

FIG. 11 illustrates, as an example for comparison, a result of measurement in the case where the tip parts 16 of the arm members 15 have been manually inserted in the channel opening 36c of the microfluidic channel 36 and the liquids 37 in the microfluidic channel 36 have been changed by a syringe pump. In FIG. 11, the horizontal axis indicates the time [sec] elapsed from the beginning of measurement, the left side vertical axis indicates the resonance frequency [Hz], and the right side vertical axis indicates Q-factor. The Q-factor is a dimensionless parameter indicating a vibration situation and relates to an energy decrease in transmission of elastic wave. In this measurement, buffer is used as the liquid 37 until 350 [sec] elapsed from the beginning, then the buffer is replaced with a solution including microtubules, and, at the time of 850 [sec] elapsed from the beginning, the solution is replaced with the buffer. The buffer is the phosphate buffered saline (PBS).

According to the result of measurement illustrated by FIG. 11, it is clear that the level of instability is higher than 1 [Hz]. Such a large instability is not suitable for any bio-sensing at the molecule level.

On the other hand, FIG. 12 illustrates a result of measurement accomplished with the molecule detecting system according to the present embodiment. In FIG. 12 (a)-(c), the horizontal axis indicates the time [sec] elapsed from the beginning of measurement, the vertical axis indicates the resonance frequency shift [Hz].

FIG. 12 (a) illustrates a resonance frequency shift continuously measured for 5 hours (18000 [sec]) elapsed from the beginning of measurement. According to this result of measurement, it is clear that, with the molecule detecting system according to the present embodiment, a result of measurement stable for hours can be obtained.

FIG. 12 (b) illustrates a resonance frequency shift in the case where the movable holding device 42 is operated by the controller 43 to accomplish a multiple moving, in which the positions of the tip parts 16 of the arm members 15 are altered into the in-liquid and the in-air positions in turns. According to this result of measurement, it is clear that, even when the positions of the tip parts 16 of the arm members 15 are altered several times into the in-liquid and the in-air positions in turns, a result of measurement stable for hours can be obtained.

FIG. 12 (c) illustrates a resonance frequency shift in case of accomplishing a multiple exchange of solution, in which the liquids 37 are altered into the deionized water (DIW) and the buffer of PBS in turns. According to this result of measurement, it is clear that, in the predetermined solution, the level of instability or the resolution of measurement is less than 20 [mHz]. This value of the resolution corresponds to the resolution of stiffness of 1 [mN/m] of the molecule bundle. 1 [mN/m] is a value corresponds to the stiffness of ten of ds DNA molecules of contour length 10 [μm]. Usually a molecular bundle contains more than a thousand of molecules. Since the value of the resolution is such a small number, it is possible to detect a mechanical interaction less than one [%] of the intrinsic bundle stiffness, which is 100 [ppm] of the maximum experienced frequency shift as illustrated in FIG. 11.

FIG. 13 illustrates a result of measurement the present inventors have accomplished with the molecule detecting system, and the result is of the case in which a variety of kinds of solutions have been used alternately as liquids 37.

FIG. 13 (a) illustrates a result of measurement continuously taken for 4 hours, and it includes the measured resonance frequency and amplitude of the arm members 15 with DNA bundles captured between their tip parts 16. In FIG. 13 (a), the horizontal axis indicates the time [sec] elapsed from the beginning of measurement, the left side vertical axis indicates the resonance frequency [Hz], and the right side vertical axis indicates the output voltage [V] of the sensor for measuring amplitude.

In this measurement, the output voltage of the sensor for measuring amplitude and the resonance frequency is continuously measured while more than 35 kinds of liquids 37 are altered. The liquids 37 are deionized water (DIW), Ni solutions of several molarity concentrations, $Zn/HNO_3$ solutions of several molarity concentrations, and buffer. The buffer is Tris (tris(hydroxymethyl)aminomethane: THAM). According to this result of measurement, it is clear that, even when many kinds of liquids 37 are altered, stable result of measurement can be obtained continuously.

FIG. 13 (b) illustrates a quantitative result of measurement of resonance frequency of the arm members 15 with DNA bundles captured between their tip parts 16 immersed in $Zn/HNO_3$ solutions of three molarity concentrations. According to this result of measurement, it is clear that DNA is relaxed in buffers and is strained in $Zn/HNO_3$ solutions or that the interaction dynamics are different in buffers and $Zn/HNO_3$ solutions.

Next will be described a result of measurement of stiffness and dumping of DNA bundle.

Figure 14:
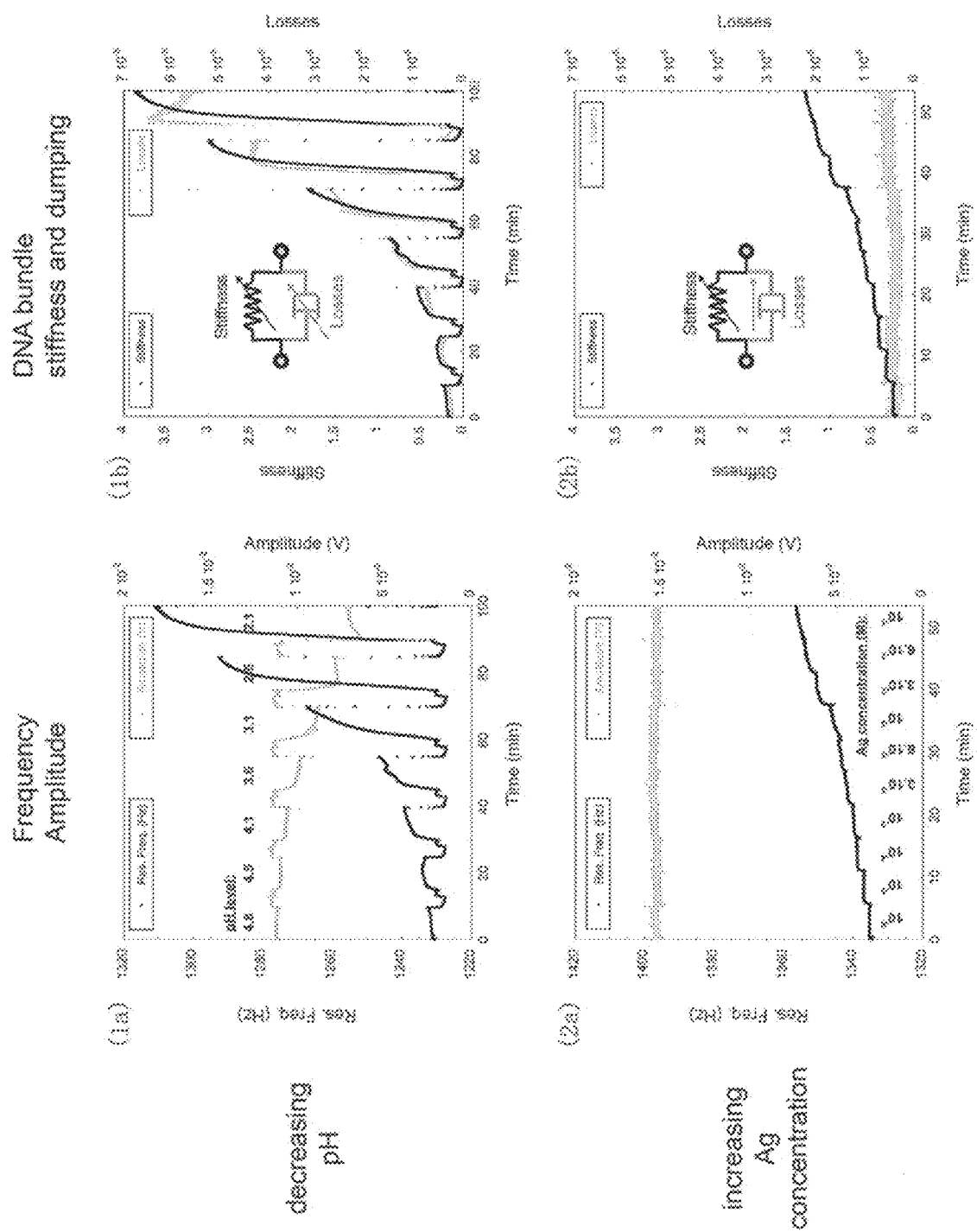
FIG. 14 is a set of graphs showing a result of measurement of stiffness and dumping of DNA bundle according to the embodiment of the present invention.

FIG. 14 is a set of graphs showing a result of measurement of stiffness and dumping of DNA bundle according to the embodiment of the present invention. In FIG. 14, (1a) and (1b) are graphs showing shifts of resonance frequency and amplitude, and shifts of stiffness and dumping in case decreasing pH of solutions, and (2a) and (2b) are graphs showing shifts of resonance frequency and amplitude, and shifts of stiffness and dumping in case increasing Ag concentration in solutions.

First the present inventors have measured, with the molecule detecting system in the present invention, the stiffness and dumping of a DNA bundle in a condition where the tip parts 16 of the arm members 15 are immersed, with the DNA bundle captured between the tip parts 16, in the liquids 37, while the liquids 37 are altered in turns from a higher pH solution to a lower pH solution in each turn.

FIG. 14 (1a) illustrates a result of measurement of the case in which the liquids 37 are altered in turns from a higher pH solution to a lower pH solution in each turn, and the result is the measured resonance frequency and amplitude of the arm members 15 with the DNA bundle captured between the tip parts 16 immersed in the liquids 37. In FIG. 14 (1a), the horizontal axis indicates the time [min] elapsed from the beginning of measurement, the left side vertical axis indicates the resonance frequency [Hz], and the right side vertical axis indicates the output voltage [V] of the sensor for measuring amplitude. Also pH values of the solutions are indicated therein. According to this result of measurement, it is clear that, as pH of solutions decreases, the resonance frequency increases and the amplitude decreases.

FIG. 14 (1b) illustrates stiffness and dumping of DNA bundle calculated based on the result illustrated in FIG. 14 (1a), according to the equivalent circuit of vibration system of the arm members 15 with DNA captured between the tip parts 16 as illustrated in FIG. 5 (a). In FIG. 14 (1b), the horizontal axis indicates the time [min] elapsed from the beginning of measurement, the left side vertical axis indicates the stiffness [N/m], and the right side vertical axis indicates the losses or damping [N·s/m]. According to this result of measurement, it is clear that, as pH of solutions decreases, the stiffness and the damping of DNA bundle increase.

FIG. 14 (2a) illustrates a result of measurement of the case in which the liquids 37 are altered in turns from a lower Ag concentration solution to a higher Ag concentration solution in each turn, and the result is the measured resonance frequency and amplitude of the arm members 15 with the DNA bundle captured between the tip parts 16 immersed in the liquids 37. In FIG. 14 (2a), the horizontal axis indicates the time [min] elapsed from the beginning of measurement, the left side vertical axis indicates the resonance frequency [Hz], and the right side vertical axis indicates the output voltage [V] of the sensor for measuring amplitude. Also Ag molarity concentration values are indicated therein. According to this result of measurement, it is clear that, as Ag concentration increases, the resonance frequency increases and the amplitude stays nearly flat.

FIG. 14 (2b) illustrates stiffness and dumping of DNA bundle calculated based on the result illustrated in FIG. 14 (2a), according to the equivalent circuit of vibration system of the arm members 15 with DNA captured between the tip parts 16 as illustrated in FIG. 5 (a). In FIG. 14 (2b), the horizontal axis indicates the time [min] elapsed from the beginning of measurement, the left side vertical axis indicates the stiffness [N/m], and the right side vertical axis indicates the losses or damping [N·s/m]. According to this result of measurement, it is clear that, as Ag concentration increases, the stiffness of DNA bundle increases and the damping of it stays nearly flat.

As described above, the present embodiment provides a molecule detecting system for detecting a reaction of a molecule captured between tip parts 16 of arm members 15 to a reagent in a liquid 37. The system comprising a nano-tweezers 10 including a couple of tip parts 16 of arm members 15 and being capable of measuring a resonance frequency and an amplitude of the tip parts 16 of the arm members 15, a microfluidic device 30 including a microfluidic channel 36 which includes a channel opening 36c on its one side, wherein an air-liquid interface the tip parts 16 can pass through is formed in the channel opening 36c, a pressure controlled microfluidic pump 33 connected to an outlet 36b of the microfluidic channel 36, a movable holding device 42 movably holding the nano-tweezers 10 or the microfluidic device 30, and a controller 43 controlling the nano-tweezers 10, the pressure controlled microfluidic pump 33, and the movable holding device 42.

Thereby, a reaction, like a biochemical reaction, of the molecule or molecule bundle of filamentary biomolecules, such as DNA, RNA, microtubule, actin, fibronectin, intermediate filament, etc. or polymers, such as polylactide, etc. to reagents, such as complementary ss DNA, drug candidates, metals, ions, nanoparticles, enzymes, etc. in the liquid 37 can be detected stably, continuously, easily, and highly repetitiously, without using any marker or labeling substance, such as fluorescent reagents. The detection is made on real time based on mechanical or electrical characteristics of the molecule or molecule bundle.

And, the nano-tweezers 10 is capable of varying a distance between the tip parts 16 at a predetermined frequency. Therefore, vibrations are applied to the molecule or molecule bundle, such as DNA, bridging the tip parts 16, so that the molecule can be characterized by measuring the resonance frequency of the molecule or molecule bundle.

Further, the tip parts 16 can be moved relatively to the channel opening 36c by the movable holding device 42 moving the nano-tweezers 10 or the microfluidic device 30, so that the tip parts 16 can be immersed in and pulled out from the liquid 37 in the microfluidic channel 36 through the air-liquid interface. Therefore, the tip parts 16 can be immersed in and pulled out from the liquid 37 automatically, stably, easily and accurately through controlling the movable holding device 42 by the controller 43.

Further, the controller 43 decides and memorizes an in-liquid position, in which the tip parts 16 are in the liquid 37, and an in-air position, in which the tip parts 16 are out of the liquid 37, through a positioning operation processed beforehand. Thereby, the tip parts 16 are always positioned in the fixed in-liquid position and the fixed in-air position by an automatic operation, so that stable and highly repetitious results of measurement can be obtained even when measurements of resonance frequency and amplitude are taken for hours or are repeated many times.

Further, the controller 43 decides the in-liquid position and the in-air position based on a change of the amplitude of the tip parts 16 of the arm members 15. Therefore, the in-liquid position and the in-air position can be decided highly accurately by an automatic operation without depending operator's senses, such as the sense of sight.

Further, the pressure controlled microfluidic pump 33 withdraws the liquid 37 in the microfluidic channel 36 from the outlet 36b, so that another liquid 37 is brought in the microfluidic channel 36 from an inlet 36a of the microfluidic channel 36. Thereby, altering of liquid 37 can be done stably in a short time.

Further, the controller 43 makes the liquid 37 in the microfluidic channel 36 altered for another liquid 37 in turns. Therefore, the reactions of the molecule or molecule bundle to many kind of reagent can be detected in a short time.

Further, the controller 43 makes a measurement of the resonance frequency and the amplitude continued, with keeping the tip parts 16, which capture the molecule, in the liquid 37, and memorizes a result of the measurement. Thereby, even when many kind of liquids 37 are altered, stable results of measurement can be obtained continuously.

Further, the controller 43 calculates a stiffness and a damping of the molecule based on the result of the measurement. Thereby, the molecule can be characterized highly accurately.

As explained above, in the molecule detecting system according to the present embodiment, any marker or labeling substance, such as fluorescent reagents, is not needed, and a continuous, stable, and highly sensitive measurement of reaction is capable, since the reaction of molecule or molecule bundle captured between a couple of the tip parts 16 of the arm members 15 is measured electrically thorough a mechanical resonance characteristic. Also, noises in measurement are reduced, and stability and repetitiousness are increased very much, since the tip parts 16 are automatically positioned and inserted in the liquid 37, and the liquid 37 is altered by the pressure controlled microfluidic pump 33. Further, interaction between the captured molecule or molecule bundle and a variety of substances can be measured.

In the molecule detecting system according to the present embodiment, since the tip parts 16 are automatically inserted in the liquid 37, motions of the tip parts 16 are highly repetitious and stable. And, since touch of the tip parts 16 on the liquid 37 or the surfaces of the PDMS film 31 etc. is detected based on changes in the amplitude of vibration, it is possible to control the position of the tip parts 16 with high precision and to detect the insertion of the tip parts 16 in the liquid 37 automatically and accurately. Further, in the molecule detecting system according to the present embodiment, since the controller 43 controls operations of the nano-tweezers 10, the pressure controlled microfluidic pump 33 and the movable holding device 42 in an integrated way, the reaction of molecule or molecule bundle captured between the tip parts 16 can be stably measured with high repetitiousness and precision. Also, the resonance frequency and the amplitude can be measured without any effect of damping of the liquid 37, since all the parts other than the tip parts 16 of the nano-tweezers 10 are always situated in the outside air.

The molecule detecting system according to the present embodiment can be applied to biological tests and can be used for an analysis of specific DNA sequences in complex solutions, such as blood samples. Also it can be applied to the pharmaceutical field and can be used for a high throughput drug screening with de novo DNA synthesis attached to the tip parts 16 to characterize DNA properties in response to chemical agents including prospective drugs or environmental agents including toxic agents. Further, it can be applied to the cancer therapy and can be used toward personalized treatment with gene therapy for chemotherapy and radiotherapy.

As described in the present embodiment, the present invention relates to a molecule detecting system whereby DNA including specific sequence is detected with high sensitivity. Therefore, it makes pathogenic detection and simple personalized gene analysis possible. And it helps the development of cancer therapy, since detection of antitumor agent reacting to DNA and measurement of DNA damage caused by radiation are made possible. Also, it can be used for detection and toxic evaluation of environmental agents, which react to DNA and cause mutation. Further, it helps the analysis and the drug development of neuropathy through the research of microtubule reaction to microtubule associated protein. Promotion of these applied researches would lead to innovative drug developments and clinical applications, and would create a very strong impact.

The present invention is not limited to the above embodiments, but may be diversely modified and varied. Thus, the modifications and variations are not excluded from the scope of protection of the present invention.

INDUSTRIAL APPLICABILITY

The present invention is applicable to a molecule detecting system.

REFERENCE SIGNS LIST

10: Nano-tweezers
16: Tip parts
30: Microfluidic device
33: Pressure controlled microfluidic pump
36: Microfluidic channel
36a: Inlet
36b: Outlet
36c: Channel opening
37: Liquid
42: Movable holding device
43: Controller

The invention claimed is:
1. A molecule detecting system for detecting a reaction of a molecule captured between electrodes to a reagent in a liquid, the system comprising:

(a) a detection device including a couple of electrodes and being capable of measuring a resonance frequency and an amplitude of the electrodes;
(b) a microfluidic device including a microfluidic channel configured for flow of a solution of reagent from an inlet to an outlet of the microfluidic channel, the microfluidic channel including a channel opening on its one side, wherein an air-liquid interface configured for the electrodes to pass through is formed in the channel opening;
(c) a pressure controlled microfluidic pump connected to the outlet of the microfluidic channel;
(d) a movable holding device movably holding the detection device or the microfluidic device; and
(e) a controller controlling the detection device, the pressure controlled microfluidic pump, and the movable holding device.

2. The molecule detecting system according to claim 1, wherein the detection device is capable of varying a distance between the electrodes at a predetermined frequency.

3. A molecule detecting system according to claim 1, wherein the electrodes can be moved relatively to the channel opening by the movable holding device moving the detection device or the microfluidic device, so that the electrodes can be immersed in and pulled out from the liquid in the microfluidic channel through the air-liquid interface.

4. The molecule detecting system according to claim 3, wherein the controller decides and memorizes an in-liquid position, in which the electrodes are in the liquid, and an in-air position, in which the electrodes are out of the liquid, through a positioning operation processed beforehand.

5. The molecule detecting system according to claim 4, wherein the controller decides the in-liquid position and the in-air position based on a change of the amplitude of the electrodes.

6. The molecule detecting system according to claim 1, wherein the pressure controlled microfluidic pump withdraws the liquid in the microfluidic channel from the outlet, so that another liquid is brought in the microfluidic channel from an inlet of the microfluidic channel.

7. The molecule detecting system according to claim 6, wherein the controller makes the liquid in the microfluidic channel altered for another liquid in turns.

8. The molecule detecting system according to claim 7, wherein the controller makes a measurement of the resonance frequency and the amplitude continued, with keeping the electrodes, which capture the molecule, in the liquid, and memorizes a result of the measurement.

9. The molecule detecting system according to claim 8, wherein the controller calculates a stiffness and a damping of the molecule based on the result of the measurement.

* * * * *